(12) United States Patent
Miyaishi et al.

(10) Patent No.: US 9,210,939 B2
(45) Date of Patent: *Dec. 15, 2015

(54) COPPER-AND-TITANIUM-CONTAINING COMPOSITION AND PRODUCTION METHOD THEREFOR

(71) Applicant: SHOWA DENKO K.K., Minato-ku, Tokyo (JP)

(72) Inventors: So Miyaishi, Toyama (JP); Yasushi Kuroda, Toyama (JP); Yasuhiro Hosogi, Toyama (JP); Ding Li, Toyama (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/002,276

(22) PCT Filed: Dec. 17, 2012

(86) PCT No.: PCT/JP2012/082707
§ 371 (c)(1),
(2) Date: Aug. 29, 2013

(87) PCT Pub. No.: WO2013/094573
PCT Pub. Date: Jun. 27, 2013

(65) Prior Publication Data
US 2014/0294989 A1    Oct. 2, 2014

(30) Foreign Application Priority Data

Dec. 22, 2011 (JP) ................. 2011-281896
May 28, 2012 (JP) ................. 2012-121345
Aug. 8, 2012 (JP) ................. 2012-175788

(51) Int. Cl.
| | |
|---|---|
| *A01N 59/16* | (2006.01) |
| *A01N 59/20* | (2006.01) |
| *B01J 23/72* | (2006.01) |
| *B01J 37/03* | (2006.01) |
| *B01J 21/06* | (2006.01) |
| *B01J 35/00* | (2006.01) |
| *A01N 55/02* | (2006.01) |
| *A61L 9/01* | (2006.01) |
| *B01J 27/055* | (2006.01) |
| *B01J 27/135* | (2006.01) |
| *B01J 27/25* | (2006.01) |
| *B01J 31/38* | (2006.01) |
| *B01J 27/122* | (2006.01) |

(52) U.S. Cl.
CPC ............... *A01N 59/16* (2013.01); *A01N 55/02* (2013.01); *A01N 59/20* (2013.01); *A61L 9/01* (2013.01); *B01J 21/063* (2013.01); *B01J 23/72* (2013.01); *B01J 27/055* (2013.01); *B01J 27/122* (2013.01); *B01J 27/135* (2013.01); *B01J 27/25* (2013.01); *B01J 31/38* (2013.01); *B01J 35/004* (2013.01); *B01J 37/033* (2013.01)

(58) Field of Classification Search
CPC .. C04B 41/4562; C04B 41/5041; A61K 8/29; A01N 59/16; A01N 59/20; B01J 21/063
See application file for complete search history.

(56) References Cited

U.S. PATENT DOCUMENTS

| | | |
|---|---|---|
| 4,591,575 A | 5/1986 | Okabayashi et al. |
| 2002/0187338 A1 | 12/2002 | Tanaka et al. |
| 2010/0040655 A1 | 2/2010 | Ren et al. |

FOREIGN PATENT DOCUMENTS

| | | | |
|---|---|---|---|
| CN | 1775347 A | 5/2006 | |
| CN | 101773841 A | 7/2010 | |
| EP | 2165762 A1 | 3/2010 | |
| EP | 2258478 A1 | 12/2010 | |
| EP | 2633907 A1 | 9/2013 | |
| JP | 11349328 | * 12/1999 | ........... C01G 23/047 |
| JP | 2000-095976 A | 4/2000 | |
| JP | 2006-232729 A | 9/2006 | |
| JP | 2009-526828 A | 7/2009 | |
| JP | 2010-168578 A | 8/2010 | |
| JP | 2011-153163 A | 8/2011 | |
| JP | 2011-190192 A | 9/2011 | |
| JP | 2012-016697 A | 1/2012 | |
| RU | 2288189 | * 11/2006 | |
| TW | 201129508 A | 9/2011 | |
| WO | 02/053501 A1 | 7/2002 | |
| WO | 2011/013850 A1 | 2/2011 | |
| WO | 2011/043496 A2 | 4/2011 | |
| WO | 2011/068094 A1 | 6/2011 | |

OTHER PUBLICATIONS

Chiang et al. (Advances in Environmental Reasearch 2002, 6, 471-485).*
Irie, Hiroshi et al., "Efficient visible light-sensitive photocatalysts: Grafting Cu(II) ions onto TiO2 and WO3 photocatalysts", Chemical Physics Letters, Elsevier B.V., Apr. 2, 2008, vol. 457, pp. 202-205.
Communication dated Sep. 9, 2014, from the European Patent Office in counterpart European Application No. 12860411.3.
K. Joseph Anthony Raj et al., "Effect of surface area, pore volume and particle size of P25 titania on the phase transformation of anatase to rutile", Indian Journal of Chemistry, Jun. 9, 2009, pp. 1378-1382, vol. 48A.
C. Karunakaran et al., "Cu-doped $TiO_2$ nanoparticles for photocatalytic disinfection of bacteria under visible light", Journal of Colloid and Interface Science, Aug. 10, 2010, pp. 68-74, vol. 352.
International Search Report for PCT/JP2012/082707 dated Jan. 29, 2013.

(Continued)

*Primary Examiner* — Abigail Fisher
*Assistant Examiner* — Jessica Kassa
(74) *Attorney, Agent, or Firm* — Sughrue Mion, PLLC

(57) ABSTRACT

The Cu- and Ti-containing composition of the present invention contains titanium oxide including rutile-crystal-type titanium oxide, and a divalent copper compound, wherein the rutile-crystal-type titanium oxide exhibits the most intense diffraction peak attributed to rutile-type titanium oxide having a full width at half maximum of 0.65° or less, in a Cu—Kα line X-ray diffraction pattern, which is obtained by plotting intensity of diffraction line with respect to diffraction angle 2θ. The composition exhibits excellent anti-viral property under light and in the dark, and excellent organic compound degradability under light.

18 Claims, 1 Drawing Sheet

(56) References Cited

OTHER PUBLICATIONS

Machine translation of JP 2009-056348 A.
Communication dated Mar. 17, 2015, issued by the State Intellectual Property Office in corresponding application No. 201280011454.8.

"Research on the impact of figure appearance, structure and modification on photocatalytic property of nanometer TiO2", Xiaohong Xia, Database of Chinese Doctoral Dissertation, vol. basic science, Issue 9, pp. 3-4 and 73-85, Sep. 15, 2008 (17 pages total).

* cited by examiner

COPPER-AND-TITANIUM-CONTAINING COMPOSITION AND PRODUCTION METHOD THEREFOR

TECHNICAL FIELD

The present invention relates to a copper- and titanium-containing composition containing titanium oxide and a copper compound, to an anti-viral agent, to a photocatalyst, and to a method for producing a copper- and titanium-containing composition.

BACKGROUND ART

Photocatalysts employing titanium oxide are widely used by virtue of low price; high chemical stability, high photocatalytic activity, such as organic compound degradability or anti-bacterial property; non-toxicity to the human body; etc.

It has been known that a mixture of titanium oxide with metallic copper or a copper compound, or a product of titanium oxide on which copper or a copper compound has been deposited, serves as an excellent photocatalyst or an excellent anti-viral agent.

For example, Patent Document 1 discloses use of nano particles of a compound $M_nX_y$ for suppression and/or prevention of infection with viruses. Examples of the nano-particle compound include $TiO_2$, $Cu_2O$, $CuO$, and combinations thereof.

Regarding the aforementioned combinations of titanium oxide with metallic copper or a copper compound, the crystal structure type of titanium oxide has been studied, and the anti-viral performance of the photocatalysts has been enhanced by use of anatase-type titanium oxide.

For example, Patent Document 2 discloses an anti-bacterial photocatalytic aqueous coating material in which a metal such as copper is deposited on a photocatalyst such as titanium oxide. Patent Document 2 also discloses that titanium oxide preferably has an anatase-type crystal structure.

Patent Document 3 discloses a phage/virus inactivating agent formed of anatase-type titanium oxide containing copper at a $CuO/TiO_2$ (ratio by mass) of 1.0 to 3.5. The invention of Patent Document 3 was accomplished with respect to the finding that copper-containing anatase-type titanium oxide can inactivate phages/viruses.

Regarding the aforementioned combinations of titanium oxide with metallic copper or a copper compound, the valency of the copper compound has been studied, and a monovalent copper compound has used as the copper compound.

Specifically, it has been known that monovalent copper exhibits excellent microorganism- and virus-inactivating performance without use of another component, whereas divalent copper has no microorganism- and virus-inactivating performance. Based on this known fact, a monovalent copper compound is used in the combination of titanium oxide with copper or a copper compound.

For example, Patent Document 4 discloses an anti-viral coating material, characterized by containing a monovalent copper compound as an active ingredient which can inactivate viruses. Patent Document 4 also discloses that the monovalent copper compound inactivates a variety of viruses through contact therewith.

Patent Document 5 discloses a microorganism inactivating agent which contains a monovalent copper compound as an active ingredient for use in inactivation of microorganisms in a short time. Patent Document 5 also discloses another microorganism inactivating agent which contains a monovalent copper compound and a photocatalytic substance. The photocatalytic substance may be a titanium oxide catalyst. Patent Document 5 further discloses that a monovalent copper compound exhibits a remarkably strong microorganism-inactivating effect, as compared with a divalent copper compound.

Patent Document 1: Japanese Kohyo (PCT) Patent Publication No. 2009-526828
Patent Document 2: Japanese Patent Application Laid-Open (kokai) No. 2000-95976
Patent Document 3: Japanese Patent Application Laid-Open (kokai) No. 2006-232729
Patent Document 4: Japanese Patent Application Laid-Open (kokai) No. 2010-168578
Patent Document 5: Japanese Patent Application Laid-Open (kokai) No. 2011-190192

Problems to be Solved by the Invention

The anti-viral agent and other materials disclosed in Patent Documents 1 to 4 were not studied in terms of anti-viral property in the dark (in the absence of irradiation with light).

Specifically, Patent Document 1 discloses examples of the nano-particle form $M_nX_y$ for suppressing infection with viruses including $TiO_2$, $Cu_2O$, $CuO$, and combinations thereof. However, the effect of suppression of infection with viruses was investigated only under light, and no study was conducted on the effect of suppression of infection with viruses in the dark.

The phage/virus inactivating agent disclosed in Patent Document 2 exhibited the inactivating effect only under irradiation with UV rays, and no study was conducted on anti-viral effect in the dark.

In Patent Document 3, $CuO/TiO_2$ samples were evaluated in terms of anti-viral effect under irradiation with UV rays (Examples 1 to 4, and Comparative Examples 3 and 4), under irradiation with visible light (Comparative Example 2), and in the dark (Comparative Example 1). Patent Document 3 discloses that "no phage inactivating effect was observed" in the dark (Comparative Example 1).

The anti-viral effect of the anti-viral coating material disclosed in Patent Document 4 was studied under a room lamp, but Patent Document 4 is silent to anti-viral effect in the dark.

Patent Document 5 discloses that a monovalent copper compound exhibits an anti-viral property in the dark, and that a composition containing the monovalent copper compound and a photocatalyst substance such as titanium oxide in combination also exhibits an anti-viral property in the dark.

However, monovalent copper compounds readily undergo oxidation. When such a monovalent copper compound is pulverized to micro-particles (200 nm or less) for imparting transparency to an object containing the copper compound, oxidation is considerably promoted. When $Cu_2O$ (red) is oxidized to CuO (black), unevenness in color arises, thereby impairing the appearance of the object.

Therefore, there is demand for development of an anti-viral agent containing a divalent copper compound and exhibiting excellent anti-viral property in the dark.

The present invention has been conceived under such circumstances. Thus, an object of the present invention is to provide a copper- and titanium-containing composition containing a divalent copper compound and titanium oxide, which composition exhibits excellent anti-viral property under light and in the dark and excellent organic compound degradability under light. Hereinafter, the composition may be referred to also as "a Cu- and Ti-containing composition." Another object is to provide an anti-viral agent. Still another object is to provide a photocatalyst. Yet another object is to provide a method for producing such a Cu- and Ti-containing composition.

Means for Solving the Problems

As described above, the following is common general technical knowledge regarding anti-viral agents containing titanium oxide and a copper compound. That is, (i) use of anatase-type titanium oxide enhances anti-viral performance (Patent Documents 2 and 3), and (ii) a monovalent copper compound exhibits excellent anti-viral performance, but a divalent copper compound has no substantial anti-viral performance (Patent Documents 4 and 5).

The present inventors have investigated the crystallinity of titanium oxide in addition to the crystal structure type thereof, and have found that use of titanium oxide having a specific crystal structure type (i.e., rutile-type) and a specific crystallinity results in anti-viral performance in the dark even when a divalent copper compound is used in combination. This finding is beyond the aforementioned common general technical knowledge. The present invention has been accomplished with respect to this finding.

Accordingly, the present invention provides the following [1] to [22].

[1] A Cu- and Ti-containing composition comprising titanium oxide including rutile-crystal-type titanium oxide, and a divalent copper compound, wherein the rutile-crystal-type titanium oxide exhibits the most intense diffraction peak attributed to rutile-type titanium oxide having a full width at half maximum of 0.65° or less, in a Cu—Kα line X-ray diffraction pattern, which is obtained by plotting intensity of diffraction line with respect to diffraction angle 2θ.

[2] A Cu- and Ti-containing composition as described in [1] above, which has a copper content, as reduced to elemental copper, of 0.1 to 20 parts by mass, with respect to 100 parts by mass of titanium oxide.

[3] A Cu- and Ti-containing composition as described in [1] or [2] above, wherein the titanium oxide has a rutile-crystal-type titanium oxide content of 15 mol % or more.

[4] A Cu- and Ti-containing composition as described in any of [1] to [3] above, wherein the titanium oxide has an anatase-type titanium oxide content less than 7 mol %.

[5] A Cu- and Ti-containing composition as described in any of [1] to [4] above, which does not contain a divalent copper compound represented by formula (1):

$$Cu_2(OH)_3X \quad (1)$$

(wherein X represents an anion).

[6] A Cu- and Ti-containing composition as described in any of [1] to [5] above, wherein the divalent copper compound is one or more species selected from the group consisting of copper oxide, a halide of divalent copper, an inorganic acid salt of divalent copper, and a carboxylic acid salt of divalent copper.

[7] A Cu- and Ti-containing composition as described in any of [1] to [6] above, wherein the divalent copper compound is one or more species selected from the group consisting of a halide of divalent copper, an inorganic acid salt of divalent copper, and a carboxylic acid salt of divalent copper.

[8] A Cu- and Ti-containing composition as described in any of [1] to [7] above, wherein the divalent copper compound is one or more species selected from the group consisting of an inorganic acid salt of divalent copper selected from among copper sulfate, copper nitrate, copper iodate, copper perchlorate, copper oxalate, copper tetraborate, copper ammonium sulfate, copper amidosulfate, copper ammonium chloride, copper pyrophosphate, and copper carbonate; a halide of divalent copper selected from among copper chloride, copper fluoride, and copper bromide; and copper oxide, copper sulfide, azurite, malachite, and copper azide.

[9] A Cu- and Ti-containing composition as described in any of [1] to [6] above, wherein the divalent copper compound is copper oxide (CuO).

[10] A Cu- and Ti-containing composition as described in any of [1] to [9] above, wherein the titanium oxide has a specific surface area of 8 to 50 m²/g.

[11] An anti-viral agent containing a composition as recited in any of [1] to [10] above.

[12] A photocatalyst containing a composition as recited in any of [1] to [10] above.

[13] A method for producing a composition as recited in any of [1] to [10] above, the method comprising a mixing step of mixing titanium oxide including rutile-crystal-type titanium oxide with a divalent copper compound raw material.

[14] A composition production method as described in [13] above, which method further comprises a heat treatment step of subjecting to a heat treatment the mixture obtained by the mixing step.

[15] A Cu- and Ti-containing composition production method as described in [13] or [14] above, wherein, in the mixing step, the titanium oxide including rutile-crystal-type titanium oxide, the divalent copper compound raw material, water, and an alkaline compound are stirred, and the stirred mixture is dehydrated.

[16] A Cu- and Ti-containing composition production method as described in any of [13] to [15] above, wherein, in the mixing step, pH is adjusted to 8 to 11.

[17] A Cu- and Ti-containing composition production method as described in any of [13] to [16] above, wherein the divalent copper compound raw material includes at least one divalent copper compound represented by formula (2):

$$CuX_2 \quad (2)$$

(wherein X represents an anion).

[18] A Cu- and Ti-containing composition production method as described in [17] above, wherein X is one member selected from among Cl, $CH_3COO$, $NO_3$, and $(SO_4)_{1/2}$.

[19] A Cu- and Ti-containing composition production method as described in any of [13] to [18] above, wherein, in the mixing step, the mixture of the titanium oxide including rutile-crystal-type titanium oxide, the divalent copper compound raw material, water, and the alkaline compound has a titanium oxide concentration of 3 to 25 mass %, with respect to the total amount of the mixture.

[20] A Cu- and Ti-containing composition production method as described in [19] above, wherein, in the mixing step, the titanium oxide and the divalent copper compound raw material are mixed with water with stirring, and the alkaline compound is added to the obtained mixture.

[21] A Cu- and Ti-containing composition production method as described in any of [13] to [20] above, which further includes, after completion of the mixing step, a heat treatment step of subjecting the composition produced by the mixing step to a heat treatment at 150 to 600° C. for 1 to 10 hours.

[22] A virus inactivation method or a deodorization method, the method comprising inactivating a virus or deodorizing by use of a Cu- and Ti-containing composition as recited in any of [1] to [10] above.

Effects of the Invention

The present invention enables provision of a Cu- and Ti-containing composition containing a divalent copper compound and titanium oxide, which composition exhibits excellent anti-viral property under light and in the dark and excellent organic compound degradability under light, an anti-viral agent, a photocatalyst, and a method for producing such a Cu- and Ti-containing composition.

MODES FOR CARRYING OUT THE INVENTION

Cu- and Ti-Containing Composition

Figure 1:
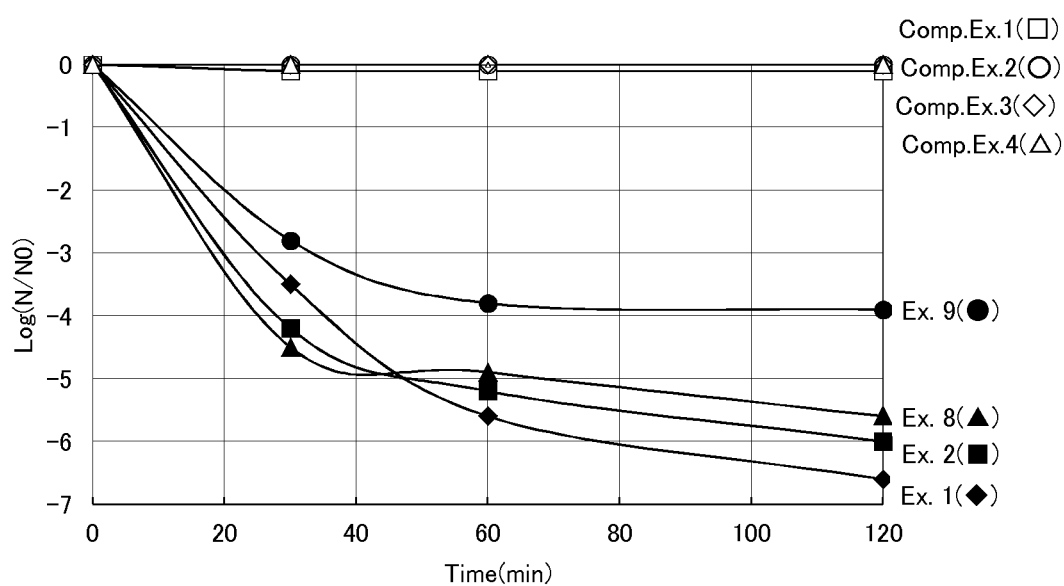
FIG. 1 A graph showing changes over time in relative phage concentration ($LOG(N/N_0)$) of samples of the Examples and Comparative Examples under light.

The Cu- and Ti-containing composition of the present invention contains titanium oxide including rutile-crystal-type titanium oxide, and a divalent copper compound, wherein the rutile-crystal-type titanium oxide exhibits the most intense diffraction peak attributed to rutile-type titanium oxide having a full width at half maximum of 0.65° or less, in a Cu—Kα line X-ray diffraction pattern, which is obtained by plotting intensity of diffraction line with respect to diffraction angle $2\theta$.

Through use, in combination, of rutile-crystal-type titanium oxide, which has rutile-type crystal form and high crystallinity, and a divalent copper compound, the Cu- and Ti-containing composition containing them exhibits excellent anti-viral property under light and in the dark and excellent organic compound degradability under light (hereinafter may be referred to as "visible-light-response"). In addition, the divalent copper compound is less likely to discolor by oxidation, differing from a monovalent copper compound. Thus, discoloration in the lapse of time can also be prevented.

As used herein, the expression "under light" refers to a milieu in the presence of visible light, and the expression "in the dark" refers to a milieu in the absence of light.

<Titanium Oxide>

The titanium oxide employed in the present invention includes rutile-crystal-type titanium oxide.

In the present invention, the "rutile-crystal-type titanium oxide" refers to a titanium oxide which exhibits the most intense diffraction peak attributed to rutile-type titanium oxide having a full width at half maximum of 0.65° or less, in a Cu—Kα line X-ray diffraction pattern, which is obtained by plotting intensity of diffraction line with respect to diffraction angle $2\theta$.

When the full width at half maximum is in excess of 0.65°, crystallinity is poor, failing to attain full anti-viral property in the dark. Thus, the full width at half maximum is preferably 0.6° or less, more preferably 0.5° or less, still more preferably 0.4° or less, yet more preferably 0.35°.

The rutile-crystal-type titanium oxide content of titanium oxide (the content may also be referred to as "rutile ratio") is preferably 15 mol % or more. When the rutile content is 15 mol % or more, the produced Cu- and Ti-containing composition exhibits satisfactory anti-viral property under light and in the dark as well as satisfactory organic compound degradability under light, in particular, satisfactory visible-light-response. Thus, the rutile ratio is more preferably 18 mol % or more, still more preferably 50 mol % or more, yet more preferably 90 mol % or more. As described hereinbelow, the rutile ratio is determined through XRD.

From the above viewpoint, the anatase-type titanium oxide content of titanium oxide (the content may also be referred to as "anatase ratio") is preferably small. Specifically, the anatase ratio is preferably less than 85 mol %, more preferably less than 82 mol %, still more preferably less than 50 mol %, yet more preferably less than 10 mol %, still more preferably less than 7 mol %, yet more preferably 0 mol % (i.e., free of anatase-type titanium oxide). The anatase ratio is also determined through XRD in a manner similar to that employed in determination of rutile ratio.

The titanium oxide preferably has a specific surface area of 1 to 200 $m^2/g$. When the specific surface area is 1 $m^2/g$ or more, contact frequency with viruses, bacteria, and organic compounds increases by virtue of such a large specific surface area. In this case, the thus-produced Cu- and Ti-containing composition exhibits excellent anti-viral property under light and in the dark, excellent organic compound degradability, and excellent anti-bacterial property. When the specific surface area is 200 $m^2/g$ or less, handling of the composition is very easy. From these viewpoints, the specific surface area of titanium oxide is more preferably 3 to 100 $m^2/g$, still more preferably 4 to 70 $m^2/g$, particularly preferably 8 to 50 $m^2/g$. The specific surface area is determined through the BET method employing nitrogen adsorption.

Generally, titanium oxide is produced through a vapor phase method or a liquid phase method. In the present invention, either titanium oxide may be used. Of these, vapor-phase-produced titanium oxide is more preferred.

In the vapor phase method, titanium tetrachloride, serving as a raw material, is caused to react with oxygen gas, to thereby yield titanium oxide. The vapor-phase-produced titanium oxide has a uniform particle size and high crystallinity, attained by high-temperature processing. As a result, the thus-produced Cu- and Ti-containing composition exhibits excellent anti-viral property under light and in the dark, excellent organic compound degradability, and excellent anti-bacterial property.

In the liquid phase method, a solution of a titanium oxide raw material, such as titanium chloride or titanyl sulfate, is hydrolyzed or neutralized, to thereby yield titanium oxide. The liquid-phase-produced titanium oxide tends to have a small rutile crystallinity and a large specific surface area. In such a case, the crystallinity and specific surface area of titanium oxide may be optimized through firing or a similar technique. However, since such a process is cumbersome, the vapor phase method is preferred.

Alternatively, a commercial product of titanium oxide may also be used as is. The alternative is advantageous, in consideration of catalyst preparation.

<Divalent Copper Compound>

The Cu- and Ti-containing composition of the present invention contains a divalent copper compound. The divalent copper compound itself has no anti-viral property under light and in the dark, no organic compound degradability under light, or no visible-light-response. However, when used in combination with the aforementioned rutile-crystal-type titanium oxide, anti-viral property under light and in the dark, organic compound degradability under light, and visible-light-response can be fully attained. The divalent copper compound is less likely to discolor by oxidation or the like, differing from a monovalent copper compound. Thus, discoloration of the Cu- and Ti-containing composition of the present invention containing the divalent copper compound can be prevented.

No particular limitation is imposed on the species of the divalent copper compound, and one or two species selected from among a divalent copper inorganic compound and a divalent copper organic compound may be used.

Examples of the divalent copper inorganic compound include one or more species selected from the group consisting of an inorganic acid salt of divalent copper selected from among copper sulfate, copper nitrate, copper iodate, copper perchlorate, copper oxalate, copper tetraborate, copper ammonium sulfate, copper amidosulfate, copper ammonium chloride, copper pyrophosphate, and copper carbonate; a halide of divalent copper selected from among copper chloride, copper fluoride, and copper bromide; and copper oxide, copper sulfide, azurite, malachite, and copper azide.

Examples of the divalent copper organic compound include divalent copper carboxylate salts. Examples of divalent copper carboxylate salts include one or more species selected from the group consisting of copper formate, copper acetate, copper propionate, copper lactate, copper valerate, copper caproate, copper enanthate, copper caprylate, copper pelargonate, copper caprate, copper myristate, copper palmitate, copper margarate, copper stearate, copper oleate, copper lactate, copper malate, copper citrate, copper benzoate, copper phthalate, copper isophthalate, copper terephthalate, copper salicylate, copper mellitate, copper oxalate, copper malonate, copper succinate, copper glutarate, copper adipate, copper fumarate, copper glycolate, copper glycerate, copper gluconate, copper tartrate, acetylacetonatocopper, ethylacetoacetonatocopper, copper isovalerate, copper β-resorcinate, copper diacetoacetate, copper formylsuccinate, copper aminosalicylate, copper bis(2-ethylhexanoate), copper sebacate, and copper naphthenate. Examples of other divalent copper organic compounds include one or more species selected from the group consisting of oxine-copper, acetylacetonatocopper, ethylacetoacetonatocopper, copper trifluoromethanesulfonate, copper phthalocyanine, copper ethoxide, copper isopropoxide, copper methoxide, and copper dimethyldithiocarbamate.

Among these divalent copper compounds, one or more species selected from among copper oxide, a divalent copper halide, a divalent copper inorganic acid salt, and a divalent copper carboxylate salt are preferred. For example, one or more species selected from among a divalent copper halide, a divalent copper inorganic acid salt, and a divalent copper carboxylate salt are preferred.

Examples of the divalent copper compound also include a divalent copper compound represented by the following formula (1):

$$Cu_2(OH)_3X \tag{1}$$

In formula (1), X represents an anion, which is preferably a halogen such as Cl, Br, or I; a carboxylic acid conjugate base such as $CH_3COO$; an inorganic acid conjugate base such as $NO_3$ or $(SO_4)_{1/2}$, or OH. However, the Cu- and Ti-containing composition of the present invention does not necessarily contain the divalent copper compound represented by formula (1) above.

Among these divalent copper compounds, a divalent copper inorganic compound is more preferred, with copper oxide being still more preferred, from the viewpoints of low impurity level and economy.

The divalent copper compound may be in the form of anhydrate or hydrate.

The divalent copper compound content, as reduced to metallic copper, is preferably 0.01 to 20 parts by mass, with respect to 100 parts by mass of the titanium oxide. When the divalent copper compound content is 0.01 parts by mass or more, anti-viral property under light and in the dark, organic compound degradability, and anti-bacterial property are favorable, whereas when the content is 20 parts by mass or less, coverage of the surfaces of titanium oxide particles is prevented, to thereby fully attain photocatalyst functions (organic compound degradability, anti-bacterial property, etc.). In this case, anti-viral performance can be enhanced by a small amount of divalent copper compound, which is economically advantageous. From this viewpoint, the divalent copper compound content, as reduced to metallic copper, is more preferably 0.1 to 20 parts by mass, still more preferably 0.1 to 15 parts by mass, yet more preferably 0.3 to 10 parts by mass, with respect to 100 parts by mass of titanium oxide.

The divalent copper compound content, as reduced to metallic copper and with respect to 100 parts by mass of the titanium oxide may be calculated from the amount of fed divalent copper compound raw material and the amount of fed titanium oxide raw material. Alternatively, the content, as reduced to metallic copper, may be determined by analyzing the Cu- and Ti-containing composition through the below-mentioned ICP (inductively coupled plasma) emission spectrophotometry.

As described above, the Cu- and Ti-containing composition of the present invention contains, as essential components, titanium oxide including rutile-crystal-type titanium oxide, and a divalent copper compound. However, the composition of the invention may optionally contain another component, so long as the object of the present invention is not impeded. In order to enhance photocatalyst functions and anti-viral performance, the essential component content of the Cu- and Ti-containing composition is preferably 90 mass % or more, more preferably 95 mass % or more, still more preferably 99 mass % or more, yet more preferably 100 mass %.

[Method of Producing Cu- and Ti-Containing Composition]

The aforementioned Cu- and Ti-containing composition may be produced by carrying out a mixing step of mixing titanium oxide including rutile-crystal-type titanium oxide with a divalent copper compound raw material, and the method is preferred. The mixture obtained by the mixing step may be subjected to a heat treatment step of heating the mixture, to thereby produce the Cu- and Ti-containing composition. Alternatively, the Cu- and Ti-containing composition may be suspending titanium oxide in an aqueous solution of a copper compound, to thereby adsorb Cu on titanium oxide.

Next, some preferred embodiments of the production method will be described.

<Production Method 1>

In Production method 1, titanium oxide including rutile-crystal-type titanium oxide, a divalent copper compound raw material, water, and an alkaline compound are mixed with stirring, and the stirred mixture is dehydrated, to thereby yield a Cu- and Ti-containing composition.

Examples of the divalent copper compound raw material include at least one divalent copper compound represented by the following formula (2):

$$CuX_2 \tag{2}$$

In formula (2), X represents an anion, which is preferably a halogen such as Cl, Br, or I; a carboxylic acid conjugate base such as $CH_3COO$; an inorganic acid conjugate base such as $NO_3$ or $(SO_4)_{1/2}$, or OH. X is more preferably at least one member selected from among Cl, $CH_3COO$, $NO_3$, and $(SO_4)_{1/2}$, still more preferably one member selected from among Cl, $CH_3COO$, $NO_3$, and $(SO_4)_{1/2}$.

Through the above procedure, the divalent copper compound raw material is hydrolyzed to form a corresponding divalent copper compound, which is then deposited on the surfaces of titanium oxide particles, whereby the aforementioned Cu- and Ti-containing composition is produced.

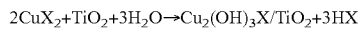

In the reaction, "$Cu_2(OH)_3X/TiO_2$" refers to a state in which $Cu_2(OH)_3X$ is deposited on $TiO_2$.

(Titanium Oxide)

As the titanium oxide of the invention, the aforementioned titanium oxide including rutile-crystal-type titanium oxide may be used. In the above reaction, the above mixture preferably has a titanium oxide concentration of 3 to 25 mass %. When the concentration is less than 3 mass %, productivity is low, which is less economy, whereas when the concentration is 25 mass % or more, the formed dispersion has excessively high viscosity, thereby making handling the mixture difficult. Both cases are not preferred.

(Divalent Copper Compound Raw Material Represented by Formula (2))

The divalent copper compound raw material represented by formula (2) may be a single-species divalent copper compound raw material (i.e., a single divalent copper compound raw material wherein X is a specific single component), or may be a mixture of two or more divalent copper compound raw materials which have different Xs and are different from one another; e.g., a mixture of $Cu(NO_3)_2$ and $Cu(OH)_2$. Alternatively, the divalent copper compound raw material represented by formula (2) may be $CuX^1X^2$ (wherein $X^2$ and $X^2$ are anions different from each other).

The divalent copper compound raw material represented by formula (2) may be in the form of anhydrate or hydrate.

The divalent copper compound raw material content, as reduced to metallic copper, is preferably 0.01 to 20 parts by mass, with respect to 100 parts by mass of the titanium oxide. When the divalent copper compound raw material content is 0.01 parts by mass or more, the anti-viral property under light and in the dark, organic compound degradability, and anti-bacterial property of the produced Cu- and Ti-containing composition are favorable, whereas when the content is 20 parts by mass or less, coverage of the surfaces of titanium oxide particles is prevented, to thereby fully attain photocatalyst functions (organic compound degradability, anti-bacterial property, etc.). In this case, anti-viral performance can be enhanced by use of a divalent copper compound raw material in a small amount, which is economically advantageous. From this viewpoint, the divalent copper compound raw material content, as reduced to metallic copper, is more preferably 0.1 to 15 parts by mass, still more preferably 0.3 to 10 parts by mass, with respect to 100 parts by mass of titanium oxide.

(Alkaline Compound)

Examples of the alkaline compound include sodium hydroxide, potassium hydroxide, tetramethylammonium hydroxide, tetrabutylammonium hydroxide, triethylamine, trimethylamine, ammonia, and a basic surfactant (e.g., BYK-9077, product of BYK Japan K.K.). Of these, sodium hydroxide is preferred. The alkaline compound is preferably added in the solution form.

The alkaline compound concentration of the solution to be added is preferably 0.1 to 5 mol/L, more preferably 0.3 to 4 mol/L, still more preferably 0.5 to 3 mol/L. A concentration in excess of 5 mol/L is not preferred, since uniform deposition fails to occur upon addition of the alkaline compound.

(Solvent)

Water is used as a solvent. However, the solvent may further contain a polar solvent other than water, so long as $CuX_2$, water, an alkaline compound, which are raw materials, can be dissolved in the solvent. Examples of the polar solvent include an alcohol, a ketone, and a mixture thereof. Examples of the alcohol include methanol, ethanol, 1-propanol, 2-propanol, and 1-butanol. Examples of other polar solvents include dimethylformamide, tetrahydrofuran, and a mixture thereof.

(Mixing and Stirring)

No particular limitation is imposed on the order of mixing and stirring of titanium oxide including rutile-crystal-type titanium oxide, a divalent copper compound raw material, water, and an alkaline compound. In one preferred mode, titanium oxide is mixed with water optionally under stirring, and then the divalent copper compound raw material is added to the mixture under stirring. In an alternative mode, the divalent copper compound raw material is mixed with water optionally under stirring, and then titanium oxide is added to the mixture under stirring. In another alternative mode, the divalent copper compound raw material and titanium oxide are simultaneously added to water, and the mixture is stirred.

The alkaline compound may be added before, during, and/or after mixing of titanium oxide and/or the copper compound raw material with water. However, preferably, the alkaline compound is added after addition of titanium oxide and the divalent copper compound raw material to water, and sufficient mixing and stirring the mixture.

No particular limitation is imposed on the stirring time, and the stirring time is, for example, about 5 to about 120 minutes, preferably about 10 to about 60 minutes. No particular limitation is imposed on the temperature at which stirring is performed, and the temperature is, for example, room temperature to about 70° C.

The mixture of titanium oxide, a divalent copper compound raw material, and water is preferably stirred at a pH of 8 to 11, when the stirring is performed at the reaction temperature. When the pH is 8 to 11, the divalent copper compound raw material is effectively hydrolyzed, whereby copper is deposited on the titanium oxide surface. In addition, the amount of alkaline compound used is reduced, making waste water treatment easy. From this viewpoint, the pH is more preferably 9 to 11, still more preferably 9.5 to 10.5. The pH is measured by means of a pH meter.

(Separation of Formed Cu- and Ti-Containing Composition)

The thus-produced Cu- and Ti-containing composition may be isolated as a solid from the liquid mixture. No particular limitation is imposed on the separation method, and examples of the method include filtration, sedimentation, centrifugation, and evaporation to dryness. Of these, separation by filtration is preferred.

If required, the thus-isolated Cu- and Ti-containing composition is subjected to washing with water, drying, pulverization, classification, etc.

<Production Method 2>

In Production method 2, titanium oxide including rutile-crystal-type titanium oxide, and a divalent copper compound raw material are dry-mixed or wet mixed, to thereby yield the aforementioned Cu- and Ti-containing composition.

In the case of wet mixing, examples of the solvent include water, an alcohol, a ketone, and a mixture thereof. Examples of the alcohol include methanol, ethanol, 1-propanol, 2-propanol, 1-butanol, and a mixture thereof. Examples of the ketone include acetone, acetylacetone, methyl ethyl ketone, and a mixture thereof. When water is used as a solvent, an aqueous solution of a copper compound is prepared in advance. The copper concentration is adjusted to several grams/100 mL to some tens of grams/100 mL (corresponding to 0.01 to 20 parts by mass with respect to titanium oxide), and then titanium oxide is suspended in the aqueous solution. The suspension is heated at about 50° C. to about 90° C., and the solid is separated through filtration, to thereby yield a Cu- and Ti-containing composition of interest. Notably, the Cu concentration and temperature are not particularly limited to those described above.

If required, the Cu- and Ti-containing composition produced through mixing is subjected to washing with water, drying, pulverization, classification, etc.

<Production Method 3>

In Production method 3, the composition produced in Production Example 1 or 2 is further subjected to a heat treatment, to thereby yield the aforementioned Cu- and Ti-containing composition. Through the heat treatment, the divalent copper compound is more firmly bonded to titanium oxide.

The heat treatment temperature is preferably 150 to 600° C. When the temperature is 150° C. or higher, sufficient bonding of the divalent copper compound can be attained, which is preferred, whereas when the temperature is 600° C. or lower, grain growth through sintering, and reduction of specific surface area can be suppressed, whereby the produced Cu- and Ti-containing composition exhibits excellent anti-viral property under light and in the dark, organic compound degradability, and anti-bacterial property. From the viewpoint, the heat treatment temperature is more preferably 200 to 500° C., still more preferably 250 to 450° C.

From the same viewpoint, the heat treatment time is preferably 1 to 10 hours, more preferably 2 to 8 hours, still more preferably 3 to 5 hours.

The heat treatment is preferably performed in an oxygen-containing atmosphere such as air.

[Anti-Viral Agent and Photocatalyst]

The aforementioned Cu- and Ti-containing composition may be used as an anti-viral agent or a photocatalyst, since the composition has an anti-viral property under light and in the dark, an organic compound degradability, and an anti-bacterial property.

[Modes of Use of Cu- and Ti-Containing Composition, Anti-Viral Agent, and Photocatalyst]

No particular limitation is imposed on the mode of use of the Cu- and Ti-containing composition, anti-viral agent, and photocatalyst of the present invention (hereinafter these may be referred to as "the Cu- and Ti-containing composition or the like of the present invention"). In one mode thereof, the composition in the solid form, such as micropowder or granules, is directly charged into an appropriate container for use. In an alternative mode, the Cu- and Ti-containing composition or the like of the present invention is incorporated into the surface and/or the inside of a substrate. Generally, the latter mode is preferred.

No particular limitation is imposed on the substrate, and examples of the substrate include a substrate formed of a single member such as metal, ceramic material, glass, etc., and a composite substrate formed of two or more members. Alternatively, the Cu- and Ti-containing composition or the like of the present invention may be incorporated into a coating agent removable by appropriate means such as a floor polish. Yet alternatively, the Cu- and Ti-containing composition or the like of the present invention is immobilized on a membrane, to thereby realize a continuous membrane on which the Cu- and Ti-containing composition or the like of the present invention is exposed to the atmosphere. Still alternatively, a thin film of the Cu- and Ti-containing composition or the like of the present invention is formed through sputtering on a titanium oxide-sputtered glass thin film. The Cu- and Ti-containing composition of the present invention may be dispersed in a solvent, to thereby provide a paint material.

One typical example of the material including a substrate, and the Cu- and Ti-containing composition or the like of the present invention immobilized on the substrate is a material including the Cu- and Ti-containing composition or the like of the present invention immobilized on a substrate by immobilization means such as a binder. The binder may be an organic binder or an inorganic binder. Of these, an inorganic binder is preferably used, for the purpose of preventing decomposition of the binder induced by a photocatalytic substance. No particular limitation is imposed on the type of the binder, any binder may be used. Examples of the binder include an inorganic binder such as a silica-based binder, which is generally used for immobilizing a photocatalytic substance onto a substrate, and a polymer binder, which can form thin film through polymerization or vaporization of solvent.

One example of a material containing the Cu- and Ti-containing composition or the like of the present invention in the substrate thereof is a material produced by hardening a resin dispersion in which the Cu- and Ti-containing composition or the like of the present invention is dispersed. Either natural resin or synthetic resin may be used. No particular limitation is imposed on the type of resin, and examples of the resin include acrylic resin, phenolic resin, polyurethane resin, acrylonitrile-styrene copolymer resin, acrylonitrile-butadiene-styrene copolymer (ABS) resin, polyester resin, and epoxy resin.

No particular limitation is imposed on the mode of use of the Cu- and Ti-containing composition or the like of the present invention, and it may be used in the presence of any light beam or in the dark. The Cu- and Ti-containing composition or the like of the present invention, which exhibits high virus-inactivating performance in the presence of water (e.g., water or sea water), under dry conditions (e.g., low-humidity conditions in, for example, winter), under high humidity conditions, or in the co-presence of organic substance, can continuously inactivate viruses. The Cu- and Ti-containing composition or the like of the present invention may be applied to any object such as a wall, floor, or ceiling; buildings such as hospitals and factories; machine tools and measuring apparatuses; inside and parts of electric appliances (inside of a refrigerator, a cloth washer, a dish washer, etc., and a filter of an air purifier). Examples of preferred dark places include the inside of a machine, a storage room of a refrigerator, a hospital facility (e.g., waiting room or surgical operation room), which is dark at night or when in a stand-by state. However, the object to which the Cu- and Ti-containing composition or the like of the present invention is applied is not particularly limited thereto. Meanwhile, there has been proposed a device having a titanium-oxide-coated ceramic or non-woven fabric filter employed in an air purifier, in combination with a light source for UV radiation, as one countermeasure against influenza. When the Cu- and Ti-containing composition or the like of the present invention is applied to such a filter, a UV light source may be omitted, thereby enhancing safety without elevating cost.

The present invention also provides a method for inactivating a virus or deodorizing by use of the aforementioned Cu- and Ti-containing composition.

EXAMPLES

The present invention will next be described in detail by way of examples, which should not be construed as limiting the invention thereto.

The properties of titanium oxide raw materials employed in the Examples and the Comparative Examples, and the produced Cu- and Ti-containing compositions were determined by the following procedures.

<Titanium Oxide Raw Materials>
(BET Specific Surface Area)

The BET specific surface area of each titanium oxide raw material was measured by means of a full-automatic BET specific surface area measuring apparatus, "Macsorb HM, model-1208," which is a product of Mountech Co., Ltd.

(Rutile Content (Rutile Ratio) and Crystallinity (Full Width at Half Maximum) of Titanium Oxide Raw Material)

The rutile-type titanium oxide content (rutile ratio) and crystallinity (full width at half maximum) of each titanium oxide raw material were determined through powder X-ray diffractometry.

Specifically, a dry titanium oxide raw material was analyzed through X-ray diffractometry by means of a diffractometer "X'pertPRO," which is a product of PANalytical, with a copper target for generating the Cu—Kα1 line. Measurement conditions included a tube voltage of 45 kV, a tube current of 40 mA, a measurement range 2θ=20 to 100°, a sampling width of 0.0167°, and a scanning speed of 3.3°/min.

The peak heights corresponding to rutile-type crystal (Hr), brookite-type crystal (Hb), and anatase-type crystal (Ha) were measured, and the rutile-type titanium oxide content (rutile ratio) of titanium oxide was determined by the following calculation formula:

Rutile ratio (mol %)={$Hr/(Ha+Hb+Hr)$}×100.

Similarly, the anatase-type titanium oxide content (anatase ratio) and brookite-type titanium oxide content (brookite ratio) of titanium oxide were determined by the following calculation formulas:

Anatase ratio (mol %)={$Ha/(Ha+Hb+Hr)$}×100

Brookite ratio (mol %)={$Hb/(Ha+Hb+Hr)$}×100.

In the X-ray diffraction pattern obtained by the X-ray diffractometry, the most intense diffraction peak attributed to rutile-type titanium oxide was selected, and the full width at half maximum at the selected peak was measured.

(Primary Particle Size)

Mean primary particle size ($D_{BET}$) (nm) was determined by measuring the specific surface area S (m²/g) of titanium oxide through the BET single point method and by use of the following equation:

$$D_{BET}=6000/(s\times\rho)$$

wherein ρ represents the density (g/cm³) of titanium oxide.

Table 1 shows the measurement results of titanium oxide raw materials employed in the Examples, Comparative Examples, and other experiments.

TABLE 1

| | Type of titanium oxide | | | | | | |
|---|---|---|---|---|---|---|---|
| | A | B | C | D | E | F | $Al_2O_3$ |
| BET (m²/g) | 10 | 20 | 20 | 100 | 150 | 100 | 40 |
| Rutile ratio (mol %) | 95.9 | 94.0 | 19.8 | 9.7 | 0.0 | 99.0 | — |
| Anatase ratio (mol %) | 4.1 | 6.0 | 80.2 | 90.3 | 36.0 | 1.0 | — |
| Brookite ratio (mol %) | 0.0 | 0.0 | 0.0 | 0.0 | 64.0 | 0.0 | — |
| Full width at half maximum (°) | 0.18 | 0.33 | 0.21 | 0.71 | — | 1.5 | — |
| Primary particle size (nm) | 150 | 75 | 75 | 15 | 10 | 15 | 50 |

Example 1

6 g (100 parts by mass) Of rutile-type titanium oxide A (product of SHOWA TITANIUM CO., LTD) was suspended in 100 mL of distilled water, and 0.0805 g (0.5 parts by mass as reduced to copper) of $CuCl_2.2H_2O$ (product of Kanto Chemical Co., Inc.) was added to the suspension, followed by stirring for 10 minutes. Then, 1-mol/L aqueous solution of sodium hydroxide (product of Kanto Chemical Co., Inc.) was added to the mixture such that pH was adjusted to 10, and the resultant mixture was stirred for 30 minutes, to thereby form a slurry. The slurry was filtered, and the recovered powder was washed with pure water, dried at 80° C., and crushed by means of a mixer, to thereby prepare a sample.

The thus-obtained sample was dissolved in hydrofluoric acid, and the solution was heated to complete dissolution. An extract of the solution was analyzed through ICP emission spectrophotometry for quantitation. As a result, 0.5 parts by mass of copper ions were deposited on 100 parts by mass of titanium oxide particles. That is, the entire amount of fed copper ions (originating from $CuCl_2.2H_2O$) was found to be deposited on the titanium oxide surface.

Example 2

The sample produced in Example 1 was heated in air at 450° C. for 3 hours, to thereby prepare another sample.

The sample was analyzed through ICP emission spectrophotometry in a manner similar to that of Example 1.

As a result, 0.5 parts by mass of copper ions were deposited on 100 parts by mass of titanium oxide particles. That is, the entire amount of fed copper ions was found to be deposited on the titanium oxide surface.

Example 3

6 g (100 parts by mass) Of rutile-type titanium oxide A was suspended in 100 mL of distilled water, and 0.1179 g (0.5 parts by mass as reduced to copper) of $CuSO_4.5H_2O$ (product of Kanto Chemical Co., Inc.) was added to the suspension, followed by stirring for 10 minutes. Subsequently, the mixture was heated to dryness at 90° C. by means of a hot stirrer, and the recovered solid was crushed by means of a mixer, to thereby produce a sample.

The sample was analyzed through ICP emission spectrophotometry in a manner similar to that of Example 1. As a result, 0.5 parts by mass of copper ions were deposited on 100 parts by mass of titanium oxide particles. That is, the entire amount of fed copper ions was found to be deposited on the titanium oxide surface.

Example 4

The procedure of Example 3 was repeated, except that 0.1179 g (0.5 parts by mass as reduced to copper) of $CuSO_4.5H_2O$ (product of Kanto Chemical Co., Inc.) was changed to 0.0805 g (0.5 parts by mass as reduced to copper) of $CuCl_2.2H_2O$ (product of Kanto Chemical Co., Inc.), to thereby produce a sample.

The sample was analyzed through ICP emission spectrophotometry in a manner similar to that of Example 1. As a result, 0.5 parts by mass of copper ions were deposited on 100 parts by mass of titanium oxide particles. That is, the entire amount of fed copper ions was found to be deposited on the titanium oxide surface.

Example 5

The procedure of Example 3 was repeated, except that 0.1179 g (0.5 parts by mass as reduced to copper) of CuSO$_4$.5H$_2$O (product of Kanto Chemical Co., Inc.) was changed to 0.1154 g (0.5 parts by mass as reduced to copper) of Cu(NO$_3$)$_2$.3H$_2$O (product of Kanto Chemical Co., Inc.), to thereby produce a sample.

The sample was analyzed through ICP emission spectrophotometry in a manner similar to that of Example 1. As a result, 0.5 parts by mass of copper ions were deposited on 100 parts by mass of titanium oxide particles. That is, the entire amount of fed copper ions was found to be deposited on the titanium oxide surface.

Example 6

The procedure of Example 3 was repeated, except that 0.1179 g (0.5 parts by mass as reduced to copper) of CuSO$_4$.5H$_2$O (product of Kanto Chemical Co., Inc.) was changed to 0.0952 g (0.5 parts by mass as reduced to copper) of Cu(CH$_3$COO)$_2$.H$_2$O (product of Kanto Chemical Co., Inc.), to thereby produce a sample.

The sample was analyzed through ICP emission spectrophotometry in a manner similar to that of Example 1. As a result, 0.5 parts by mass of copper ions were deposited on 100 parts by mass of titanium oxide particles. That is, the entire amount of fed copper ions was found to be deposited on the titanium oxide surface.

Reference Example 7

3 g Of CuCl$_2$.2H$_2$O (product of Kanto Chemical Co., Inc.) was suspended in 100 mL of distilled water, and the suspension was stirred for 10 minutes. Then, 1-mol/L aqueous solution of sodium hydroxide (product of Kanto Chemical Co., Inc.) was added to the suspension such that pH was adjusted to 10, and the resultant mixture was stirred for 30 minutes, to thereby form a slurry. The slurry was filtered, and the recovered powder was washed with pure water, dried at 80° C., and crushed by means of a mixer, to thereby prepare a Cu$_2$(OH)$_3$Cl single phase.

The Cu$_2$(OH)$_3$Cl single phase in an amount of 0.0504 g (0.5 parts by mass as reduced to copper) was mixed with 6 g (100 parts by mass) of rutile-type titanium oxide A by means of an agate mortar for 30 minutes for pulverization, to thereby produce a sample.

Example 8

The procedure of Example 1 was repeated, except that rutile-type titanium oxide B (product of SHOWA TITANIUM CO., LTD) was used instead of rutile-type titanium oxide A (product of SHOWA TITANIUM CO., LTD), to thereby produce a sample.

The sample was analyzed through ICP emission spectrophotometry in a manner similar to that of Example 1. As a result, 0.5 parts by mass of copper ions were deposited on 100 parts by mass of titanium oxide particles. That is, the entire amount of fed copper ions was found to be deposited on the titanium oxide surface.

Reference Example 9

The procedure of Example 1 was repeated, except that rutile-type titanium oxide C (product of SHOWA TITANIUM CO., LTD) was used instead of rutile-type titanium oxide A (product of SHOWA TITANIUM CO., LTD), to thereby produce a sample.

The sample was analyzed through ICP emission spectrophotometry in a manner similar to that of Example 1. As a result, 0.5 parts by mass of copper ions were deposited on 100 parts by mass of titanium oxide particles. That is, the entire amount of fed copper ions was found to be deposited on the titanium oxide surface.

Reference Example 10

The procedure of Example 1 was repeated, except that the amount of CuCl$_2$.2H$_2$O (product of Kanto Chemical Co., Inc.) was changed to 0.0161 g (0.1 parts by mass as reduced to copper), to thereby produce a sample.

The sample was analyzed through ICP emission spectrophotometry in a manner similar to that of Example 1. As a result, 0.1 parts by mass of copper ions were deposited on 100 parts by mass of titanium oxide particles. That is, the entire amount of fed copper ions was found to be deposited on the titanium oxide surface.

Example 11

The procedure of Example 1 was repeated, except that the amount of CuCl$_2$.2H$_2$O (product of Kanto Chemical Co., Inc.) was changed to 0.8048 g (5 parts by mass as reduced to copper), to thereby produce a sample.

The sample was analyzed through ICP emission spectrophotometry in a manner similar to that of Example 1. As a result, 5 parts by mass of copper ions were deposited on 100 parts by mass of titanium oxide particles. That is, the entire amount of fed copper ions was found to be deposited on the titanium oxide surface as CuO.

Comparative Example 1

The procedure of Example 1 was repeated, except that anatase-type titanium oxide D (product of SHOWA TITANIUM CO., LTD) was used instead of rutile-type titanium oxide A (product of SHOWA TITANIUM CO., LTD), to thereby produce a sample.

The sample was analyzed through ICP emission spectrophotometry in a manner similar to that of Example 1. As a result, 0.5 parts by mass of copper ions were deposited on 100 parts by mass of titanium oxide particles. That is, the entire amount of fed copper ions was found to be deposited on the titanium oxide surface.

Comparative Example 2

The sample produced in Comparative Example 1 was heated in air at 450° C. for 3 hours, to thereby prepare another sample.

Comparative Example 3

The procedure of Example 1 was repeated, except that brookite-type titanium oxide E (product of SHOWA TITANIUM CO., LTD) was used instead of rutile-type titanium oxide A (product of SHOWA TITANIUM CO., LTD), to thereby produce a sample.

The sample was analyzed through ICP emission spectrophotometry in a manner similar to that of Example 1. As a result, 0.5 parts by mass of copper ions were deposited on 100 parts by mass of titanium oxide particles. That is, the entire amount of fed copper ions was found to be deposited on the titanium oxide surface.

Comparative Example 4

The procedure of Example 1 was repeated, except that rutile-type titanium oxide F (product of SHOWA TITANIUM CO., LTD) was used instead of rutile-type titanium oxide A (product of SHOWA TITANIUM CO., LTD, to thereby produce a sample.

The sample was analyzed through ICP emission spectrophotometry in a manner similar to that of Example 1. As a result, 0.5 parts by mass of copper ions were deposited on 100 parts by mass of titanium oxide particles. That is, the entire amount of fed copper ions was found to be deposited on the titanium oxide surface.

Comparative Example 5

The procedure of Example 1 was repeated, except that aluminum oxide ($Al_2O_3$, product of Aldrich) was used instead of rutile-type titanium oxide A (product of SHOWA TITANIUM CO., LTD), to thereby produce a sample.

The sample was analyzed through ICP emission spectrophotometry in a manner similar to that of Example 1. As a result, 0.5 parts by mass of copper ions were deposited on 100 parts by mass of aluminum oxide particles. That is, the entire amount of fed copper ions was found to be deposited on the aluminum oxide surface.

Comparative Example 6

5 g (100 parts by mass) Of rutile-type titanium oxide A (product of SHOWA TITANIUM CO., LTD) and 0.025 g (0.5 parts by mass) of copper (product of Kanto Chemical Co., Inc.) were mixed by means of an agate mortar for 30 minutes for pulverization, to thereby produce a sample.

Comparative Example 7

6 g (100 parts by mass) Of rutile-type titanium oxide A (product of SHOWA TITANIUM CO., LTD) was suspended in 100 mL of distilled water, and 0.0805 g (0.5 parts by mass as reduced to copper) of $CuCl_2.2H_2O$ (product of Kanto Chemical Co., Inc.) was added to the suspension, followed by stirring for 10 minutes. Then, 1-mol/L aqueous solution of sodium hydroxide (product of Kanto Chemical Co., Inc.) was added to the mixture such that pH was adjusted to 10. Then, 12.0 mL of 0.01-mol/L aqueous hydrazine (product of Kanto Chemical Co., Inc.) was added to the mixture, so that the ratio by mole $CuCl_2.2H_2O:N_2H_4$ was adjusted to 1:0.25, and the resultant mixture was stirred for 30 minutes, to thereby form a slurry. The slurry was filtered, and the recovered powder was washed with pure water, dried at 80° C., and crushed by means of a mixer, to thereby prepare a sample, in which CuO was deposited on the rutile-type titanium oxide A particles.

The thus-obtained sample was dissolved in hydrofluoric acid, and the solution was heated to complete dissolution. An extract of the solution was analyzed through ICP emission spectrophotometry for quantitation. As a result, 0.5 parts by mass of copper ions were deposited on 100 parts by mass of titanium oxide particles. That is, the entire amount of fed copper ions (originating from $CuCl_2.2H_2O$) was found to be deposited on the titanium oxide surface.

Comparative Example 8

Rutile-type titanium oxide A (product of SHOWA TITANIUM CO., LTD) was used as a sample.

<Measurement>
(Rutile-Type Titanium Oxide Content (Rutile Ratio) and Crystallinity (Full Width at Half Maximum))

The rutile-type titanium oxide content (rutile ratio) and crystallinity (full width at half maximum) of each of the samples produced in the Examples and the Comparative Examples were determined through powder X-ray diffractometry.

Specifically, a dry Cu- and Ti-containing composition was ground by means of an agate mortar, to thereby prepare a powder sample. The sample was analyzed through X-ray diffractometry by means of a diffractometer "X'pertPRO," which is a product of PANalytical, with a copper target for generating the Cu—Kα1 line. Measurement conditions included a tube voltage of 45 kV, a tube current of 40 mA, a measurement range 2θ=20 to 100°, a sampling width of 0.0167°, and a scanning speed of 3.3°/min.

The peak heights corresponding to rutile-type crystal (Hr), brookite-type crystal (Hb), and anatase-type crystal (Ha) were measured, and the rutile-type titanium oxide content (rutile ratio) of titanium oxide was determined by the following calculation formula:

Rutile ratio (mol %)=$\{Hr/(Ha+Hb+Hr)\} \times 100$.

In the X-ray diffraction pattern obtained by the X-ray diffractometry, the most intense diffraction peak attributed to rutile-type titanium oxide was selected, and the full width at half maximum at the selected peak was measured. Table 2 shows the results.

(Identification of Divalent Copper Compounds)

Divalent copper compounds present in the samples of the Examples and the Comparative Examples were identified through X-ray diffractometry by means of the aforementioned diffractometer under the aforementioned conditions. Table 2 shows the results.

(Evaluation of Anti-Viral Performance Under Light: Determination of $LOG(N/N_0)$)

The anti-viral performance of the samples of the Examples and the Comparative Examples was assessed through the following model experiment employing bacteriophage. Notably, assessment of anti-viral performance with respect to inactivation performance with respect to bacteriophage is disclosed in, for example, Appl. Microbiol. Biotechnol., 79, pp. 127-133, 2008. The bacteriophage inactivation performance is known as a reliable model for the assessment.

A filter paper piece was placed on the bottom of a deep Petri dish, and a small amount of sterilized water was added to the Petri dish. A glass base plate having a thickness of about 5 mm was placed on the filter paper piece. On the glass base plate, there was placed a glass plate (50 mm×50 mm×1 mm) onto which each of the samples of the Examples and the Comparative Examples in an amount of 5 mg had been applied. 100 μL of QBphage (NBRC20012) suspension which had been acclimated in advance and whose concentration had been determined was added dropwise to the glass plate. In order to bring the sample surface into contact with the phage, the glass plate was covered with OHP film made of PET (polyethylene terephthalate). A glass lid was put on the deep Petri dish, to thereby provide a measurement unit. Regarding each sample, a plurality of measurement units were provided.

A 15 W white fluorescent lamp (Full white fluorescent lamp, FL15N, product of Panasonic Corporation) equipped with a UV-cutting filter (N-113, product of Nitto Jushi Kogyo Co., Ltd.) was employed as a light source. The aforementioned measurement units were placed under the light source at a position where the illuminance (measured by means of an illuminometer: TOPCON IM-5) was 800 lx. After the elapse of a predetermined time, the phage concentration of each sample present on the glass plate was measured.

Phage concentration was determined through the following procedure. The sample present on the glass plate was recovered with 9.9 mL of a phage recovery liquid (phosphate buffered saline), and the liquid was shaken by means of a shaker for 10 minutes. The phage-recovered liquid was appropriately diluted, and the dilution was mixed with a separately prepared *E. coli* (NBRC 13965) culture liquid ($OD_{600}$>1.0, 1×10$^8$ CFU/mL) under stirring. Thereafter, the mixture was allowed to stand in a thermostat container at 37° C. for 10 minutes, to thereby infect *E. coli* with the phage. The resultant liquid was added to an agar medium, and culturing was performed at 37° C. for 15 hours. The number of plaques of the phage was visually counted. The phage concentration N was derived through multiplication of the count by the dilution factor of the phage-recovered liquid.

From the initial phage concentration $N_0$ and phage concentrations N after the elapse of a predetermined time, the relative phage concentration ($LOG(N/N_0)$) was determined. Table 2 and FIG. 1 show the results.

The smaller the $LOG(N/N_0)$, the stronger the anti-viral property.

(Evaluation of Anti-Viral Performance in the Dark: Determination of $LOG(N/N_0)$)

Figure 2:
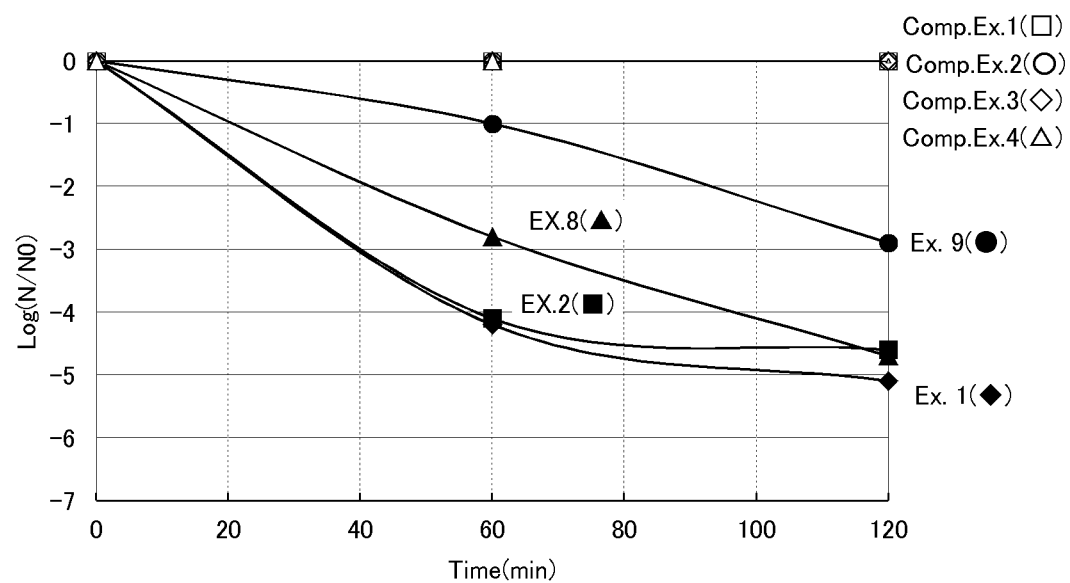
FIG. 2 A graph showing changes over time in relative phage concentration ($LOG(N/N_0)$) of samples of the Examples and Comparative Examples in the dark.

The procedure of "Evaluation of anti-viral performance under light: determination of $LOG(N/N_0)$" was repeated, except that measurement units were placed in the dark without irradiation with light from the light source. Table 2 and FIG. 2 show the results.

The smaller the $LOG(N/N_0)$, the stronger the anti-viral property.

(Evaluation of Volatile Organic Compound (VOC) Decomposition Activity Under Light: Measurement of $CO_2$ Generation Amount)

In a sealable glass reactor (capacity: 0.5 L), glass Petri dishes each having a diameter of 1.5 cm were placed. On each Petri dish, 0.1 g of each of the samples produced in the Examples and the Comparative Examples was placed. The atmosphere inside the reactor was substituted by a mixture of oxygen and nitrogen with a volume ratio of 1:4. To the reactor, 5.2 µL of water (corresponding to a relative humidity of 50% (25° C.)), and 5.0 mL of 5.1 vol. % acetaldehyde standard gas (mixture with nitrogen, standard temperature and pressure (25° C., 1 atm)) were added, and the reactor was closed (acetaldehyde concentration in the glass reactor adjusted to 500 ppm by volume). The reactor was irradiated with visible light.

Irradiation with visible light was carried out by means of a light source including a xenon lamp equipped with a filter which cuts UV rays having a wavelength of 400 nm or shorter (trade name: L-42, AGC Techno Glass Co., Ltd.). The light source was set so that the illuminance in the reactor was adjusted to 100,000 lx. The rate of decrease of acetaldehyde, and the rate of generation of carbon dioxide, which is a decomposition product via oxidation, were monitored through gas chromatography. Table 2 shows the $CO_2$ generation amount (ppm by mass) 3 hours after a start of irradiation with visible light.

The greater the $CO_2$ generation amount (ppm by mass), the higher the volatile organic compound (VOC) decomposition activity.

TABLE 2

| | Raw materials | | | | | |
|---|---|---|---|---|---|---|
| | Ti oxide raw material or Al oxide | | | | Cu compd. or Cu metal | |
| | Type | Rutile ratio (mol/%) | Full width at half max. (°) | Parts by mass | Type | Cu parts by mass |
| Ex. 1 | A | 95.9 | 0.18 | 99.5 | $CuCl_2 \cdot 2H_2O$ | 0.5 |
| Ex. 2 | A | 95.9 | 0.18 | 99.5 | $CuCl_2 \cdot 2H_2O$ | 0.5 |
| Ex. 3 | A | 95.9 | 0.18 | 99.5 | $CuSO_4 \cdot 5H_2O$ | 0.5 |
| Ex. 4 | A | 95.9 | 0.18 | 99.5 | $CuCl_2 \cdot 2H_2O$ | 0.5 |
| Ex. 5 | A | 95.9 | 0.18 | 99.5 | $Cu(NO_3)_2 \cdot 3H_2O$ | 0.5 |
| Ex. 6 | A | 95.9 | 0.18 | 99.5 | $Cu(CH_3COO)_2 \cdot H_2O$ | 0.5 |
| Ref. Ex. 7 | A | 95.9 | 0.18 | 99.5 | $CuCl_2 \cdot 2H_2O$ | 0.5 |
| Ex. 8 | B | 94.0 | 0.33 | 99.5 | $CuCl_2 \cdot 2H_2O$ | 0.5 |
| Ref. Ex. 9 | C | 19.8 | 0.21 | 99.5 | $CuCl_2 \cdot 2H_2O$ | 0.5 |
| Ref. Ex. 10 | A | 95.9 | 0.18 | 99.9 | $CuCl_2 \cdot 2H_2O$ | 0.1 |
| Ex. 11 | A | 95.9 | 0.18 | 95.0 | $CuCl_2 \cdot 2H_2O$ | 5.0 |
| Comp. Ex. 1 | D | 9.7 | 0.71 | 100 | $CuCl_2 \cdot 2H_2O$ | 0.5 |
| Comp. Ex. 2 | D | 9.7 | 0.71 | 100 | $CuCl_2 \cdot 2H_2O$ | 0.5 |
| Comp. Ex. 3 | E | 0.0 | — | 100 | $CuCl_2 \cdot 2H_2O$ | 0.5 |
| Comp. Ex. 4 | F | 99.0 | 1.50 | 100 | $CuCl_2 \cdot 2H_2O$ | 0.5 |
| Comp. Ex. 5 | $Al_2O_3$ | — | — | 100 | $CuCl_2 \cdot 2H_2O$ | 0.5 |
| Comp. Ex. 6 | A | 95.9 | 0.18 | 100 | Cu | 0.5 |
| Comp. Ex. 7 | A | 95.9 | 0.18 | 100 | $CuCl_2 \cdot 2H_2O$ | 0.5 |
| Comp. Ex. 8 | A | 95.9 | 0.18 | 100 | — | — |

| | Cu- and Ti-contg. compd. | | | | Anti-viral property (light) LOG(N/N0) [/min irradn.] | | | Anti-viral property (dark) LOG(N/N0) [/min irradn.] | | VOC decompn. activity $CO_2$ generation (3 h) [/ppm] |
|---|---|---|---|---|---|---|---|---|---|---|
| | Ti oxide | | | | | | | | | |
| | Rutile ratio (mol/%) | Full width at half max. (°) | Cu compd. Type | Deposit or single phase | 30 | 60 | 120 | 60 | 120 | Under light |
| Ex. 1 | 95.9 | 0.18 | $Cu_2(OH)_3Cl$ | deposit | −3.5 | −5.6 | −6.6 | −4.2 | −5.1 | 144 |
| Ex. 2 | 95.9 | 0.18 | CuO | deposit | −4.2 | −5.2 | −6.0 | −4.1 | −4.6 | 165 |
| Ex. 3 | 95.9 | 0.18 | $CuSO_4 \cdot 5H_2O$ | deposit | −4.0 | −5.9 | −6.2 | −4.0 | −4.7 | 84 |

TABLE 2-continued

| | | | | | | | | | | | |
|---|---|---|---|---|---|---|---|---|---|---|---|
| Ex. 4 | 95.9 | 0.18 | CuCl$_2$•2H$_2$O | deposit | | -2.0 | -3.1 | -5.7 | -1.0 | -1.7 | 22 |
| Ex. 5 | 95.9 | 0.18 | Cu(NO$_3$)$_2$•3H$_2$O | deposit | | -3.5 | -4.2 | -6.0 | -3.1 | -4.2 | 53 |
| Ex. 6 | 95.9 | 0.18 | Cu(CH$_3$COO)$_2$•H$_2$O | deposit | | -3.1 | -3.9 | -5.2 | -2.5 | -3.4 | 34 |
| Ref. Ex. 7 | 95.9 | 0.18 | Cu$_2$(OH)$_3$Cl | mix | | -3.8 | -4.5 | -5.4 | -3.5 | -4.0 | 0 |
| Ex. 8 | 94.0 | 0.33 | Cu$_2$(OH)$_3$Cl | deposit | | -4.5 | -4.9 | -5.6 | -2.8 | -4.7 | 202 |
| Ref. Ex. 9 | 19.8 | 0.21 | Cu$_2$(OH)$_3$Cl | deposit | | -2.8 | -3.8 | -3.9 | -1.0 | -2.9 | 136 |
| Ref. Ex. 10 | 95.9 | 0.18 | Cu$_2$(OH)$_3$Cl | deposit | | -1.3 | -1.8 | -2.6 | -1.5 | -1.3 | 318 |
| Ex. 11 | 95.9 | 0.18 | Cu$_2$(OH)$_3$Cl | deposit | | -4.1 | -6.9 | -6.9 | -4.6 | -6.6 | 169 |
| Comp. Ex. 1 | 9.7 | 0.71 | Cu$_2$(OH)$_3$Cl | deposit | | -0.1 | -0.1 | -0.1 | 0.0 | 0.0 | 102 |
| Comp. Ex. 2 | 9.7 | 0.71 | CuO | deposit | | 0.0 | 0.0 | 0.0 | 0.0 | 0.0 | 96 |
| Comp. Ex. 3 | 0.0 | — | Cu$_2$(OH)$_3$Cl | deposit | | 0.0 | 0.0 | 0.0 | 0.0 | 0.0 | 112 |
| Comp. Ex. 4 | 99.0 | 1.50 | Cu$_2$(OH)$_3$Cl | deposit | | 0.0 | 0.0 | 0.0 | 0.0 | 0.0 | 160 |
| Comp. Ex. 5 | — | — | Cu$_2$(OH)$_3$Cl | deposit | | 0.0 | 0.0 | 0.0 | 0.0 | 0.0 | 0 |
| Comp. Ex. 6 | 95.9 | 0.18 | Cu | mix | | -0.5 | -1.5 | -1.8 | -0.2 | -0.5 | 190 |
| Comp. Ex. 7 | 95.9 | 0.18 | Cu$_2$O | deposit | | -2.4 | -4.6 | -5.9 | -3.4 | -4.2 | 138 |
| Comp. Ex. 8 | 95.9 | 0.18 | — | — | | -0.1 | -0.6 | -1.2 | 0.0 | -0.1 | 205 |

<Results>

Through comparison of the Examples with the Comparative Examples, the Cu- and Ti-containing composition of the present invention exhibits excellent anti-viral property under light and in the dark, and excellent organic compound degradability under light. In addition, since the composition of the present invention contains a divalent copper compound instead of a monovalent copper compound, discoloration by oxidation or other reasons can be prevented, thereby providing favorable design.

Also through comparison of Example 1 with Example 2, through carrying out heat treatment, bonding between the divalent copper compound and titanium oxide can be more strengthened, while high anti-phage is maintained.

The invention claimed is:

1. A Cu- and Ti-containing composition comprising titanium oxide including rutile-crystal-type titanium oxide, and a divalent copper compound, wherein the rutile-crystal-type titanium oxide exhibits the most intense diffraction peak attributed to rutile-type titanium oxide having a full width at half maximum of 0.65° or less, in a Cu—Kα line X-ray diffraction pattern, which is obtained by plotting intensity of diffraction line with respect to diffraction angle 2θ,
   wherein the rutile-crystal-type titanium oxide content of titanium oxide is 50 mol % or more and the anatase-type titanium oxide content of titanium oxide is less than 50 mol %,
   wherein the titanium oxide has a specific surface area of 8 to 50 m$^2$/g,
   wherein the divalent copper compound is deposited on a surface of the titanium oxide,
   wherein a copper content, as reduced to elemental copper, of the divalent copper compound is 0.3 to 10 parts by mass with respect to 100 parts by mass of titanium oxide, and
   wherein the titanium oxide has a rutile-crystal-type titanium oxide content of 90 mol % or more.

2. A Cu- and Ti-containing composition according to claim 1, wherein the titanium oxide has an anatase-type titanium oxide content less than 7 mol %.

3. A Cu- and Ti-containing composition according to claim 1, which does not contain a divalent copper compound represented by formula (1):

$$Cu_2(OH)_3X \qquad (1)$$

(wherein X represents an anion).

4. A Cu- and Ti-containing composition according to claim 1, wherein the divalent copper compound is one or more species selected from the group consisting of copper oxide, a halide of divalent copper, an inorganic acid salt of divalent copper, and a carboxylic acid salt of divalent copper.

5. A Cu- and Ti-containing composition according to claim 1, wherein the divalent copper compound is one or more species selected from the group consisting of a halide of divalent copper, an inorganic acid salt of divalent copper, and a carboxylic acid salt of divalent copper.

6. A Cu- and Ti-containing composition according to claim 1, wherein the divalent copper compound is one or more species selected from the group consisting of an inorganic acid salt of divalent copper selected from among copper sulfate, copper nitrate, copper iodate, copper perchlorate, copper oxalate, copper tetraborate, copper ammonium sulfate, copper amidosulfate, copper ammonium chloride, copper pyrophosphate, and copper carbonate; a halide of divalent copper selected from among copper chloride, copper fluoride, and copper bromide; and copper oxide, copper sulfide, azurite, malachite, and copper azide.

7. A Cu- and Ti-containing composition according to claim 1, wherein the divalent copper compound is copper oxide (CuO).

8. An anti-viral agent containing the Cu- and Ti-containing composition as recited in claim 1.

9. A photocatalyst containing the Cu- and Ti-containing composition as recited in claim 1.

10. A method for producing the Cu- and Ti-containing composition as recited in claim 1, the method comprising a mixing step of mixing titanium oxide including rutile-crystal-type titanium oxide with a divalent copper compound raw material.

11. A Cu- and Ti-containing composition production method according to claim 10, which method further comprises a heat treatment step of subjecting to a heat treatment the mixture obtained by the mixing step.

12. A Cu- and Ti-containing composition production method according to claim 10, wherein, in the mixing step, the titanium oxide including rutile-crystal-type titanium oxide, the divalent copper compound raw material, water, and an alkaline compound are stirred, and the stirred mixture is dehydrated.

13. A Cu- and Ti-containing composition production method according to claim 10, wherein, in the mixing step, pH is adjusted to 8 to 11.

14. A Cu- and Ti-containing composition production method according to claim 10, wherein the divalent copper compound raw material includes at least one divalent copper compound represented by formula (2):

$$CuX_2 \qquad (2)$$

(wherein X represents an anion).

15. A Cu- and Ti-containing composition production method according to claim 14, wherein X is one member selected from among Cl, $CH_3COO$, $NO_3$, and $(SO_4)_{1/2}$.

16. A Cu- and Ti-containing composition production method according to claim 12, wherein, in the mixing step, the mixture of the titanium oxide including rutile-crystal-type titanium oxide, the divalent copper compound raw material, water, and the alkaline compound has a titanium oxide concentration of 3 to 25 mass %, with respect to the total amount of the mixture.

17. A Cu- and Ti-containing composition production method according to claim 12, wherein, in the mixing step, the titanium oxide and the divalent copper compound raw material are mixed with water with stirring, and the alkaline compound is added to the obtained mixture.

18. A Cu- and Ti-containing composition production method according to claim 10, which further includes, after completion of the mixing step, a heat treatment step of subjecting the composition produced by the mixing step to a heat treatment at 150 to 600° C. for 1 to 10 hours.

* * * * *